(12) United States Patent
Goldfarb

(10) Patent No.: US 11,759,636 B2
(45) Date of Patent: Sep. 19, 2023

(54) APPARATUS AND METHOD FOR TREATING OBSTRUCTIVE SLEEP APNEA

(71) Applicant: David Goldfarb, Naples, FL (US)

(72) Inventor: David Goldfarb, Naples, FL (US)

(*) Notice: Subject to any disclaimer, the term of this patent is extended or adjusted under 35 U.S.C. 154(b) by 431 days.

(21) Appl. No.: 16/985,530

(22) Filed: Aug. 5, 2020

(65) Prior Publication Data
US 2021/0038891 A1 Feb. 11, 2021

Related U.S. Application Data

(60) Provisional application No. 62/922,341, filed on Aug. 5, 2019.

(51) Int. Cl.
*A61N 1/36* (2006.01)
*A61M 16/00* (2006.01)

(52) U.S. Cl.
CPC ........ *A61N 1/36031* (2017.08); *A61N 1/3601* (2013.01); *A61M 16/0003* (2014.02)

(58) Field of Classification Search
CPC .............. A61N 1/36031; A61N 1/3601; A61N 1/0452; A61N 1/0456; A61M 16/0003; A61M 2205/054; A61M 2230/205; A61M 16/06
See application file for complete search history.

(56) References Cited

U.S. PATENT DOCUMENTS

| | | | |
|---|---|---|---|
| 5,111,814 A | 5/1992 | Goldfarb | |
| 2005/0288729 A1* | 12/2005 | Libbus | A61N 1/3601 607/42 |
| 2008/0269832 A1 | 10/2008 | Wong et al. | |
| 2015/0073232 A1* | 3/2015 | Ahmad | A61B 5/11 607/42 |
| 2020/0238084 A1* | 7/2020 | Ignagni | A61N 1/3601 |

FOREIGN PATENT DOCUMENTS

EP 1277491 B1 1/2008

OTHER PUBLICATIONS

Joerg Steier et al. "Continuous Transcutaneous Submental Electrical Stimulation in Obstructive Sleep Apnea", Chest Journal, Oct. 2011, pp. 998-1007, vol. 140, Issue 4, https://journal.chestnet.org/article/S0012-3692(11)60537-0/fulltext#relatedArticles.
Ghimire, P., et al., "Pickwickian Syndrome", StatPearls Publishing, Jul. 2020, https://www.ncbi.nlm.nih.gov/books/NBK542216/.
(Continued)

*Primary Examiner* — Amanda K Hulbert
*Assistant Examiner* — Philip C Edwards
(74) *Attorney, Agent, or Firm* — Steven J. Rocci P.C.

(57) ABSTRACT

An apparatus and method for treating obstructive sleep apnea includes a pulse oximeter, a source of transcutaneous electrical stimulation having a pair of electrodes for delivering TES to a person, and a controller. The electrodes are adapted to be applied to the person's skin adjacent the person's upper airway to stimulate one or more nerves or muscles in the upper airway when TES is applied to the electrodes. The controller is adapted to receive blood oxygen data from the pulse oximeter and is programmed to apply TES when the blood oxygen indicates that the person's blood oxygen is below a predetermined threshold, so as to increase a resting tone of the person's tongue.

6 Claims, 7 Drawing Sheets

(56) References Cited

OTHER PUBLICATIONS

Masa, Juan F. et al., "Efficacy of Different Treatment Alternatives for Obesity Hypoventilation Syndrome. Pickwick Study.", American Journal of Respiratory and Critical Care Medicine, Jul. 2015, vol. 192, Issue 1, pp. 86-95, https://pubmed.ncbi.nlm.nih.gov/25915102/.

Wray, Christina M., et al., "Hypoglossal nerve stimulation for obstructive sleep apnea: A review of the literature", World Journal of Otorhinolaryngology—Head and Neck Surgery, Dec. 2016, vol. 2, Issue 4, pp. 230-233, https://www.sciencedirect.com/science/article/pii/S2095881116300737.

Pengo, Martino F., et al., "Emerging technology: electrical stimulation in obstructive sleep apnoea", JTD Journal of Thoracic Disease, Aug. 2015, vol. 7, Issue 8, http://jtd.amegroups.com/article/view/2429/5199.

Fogel, Robert B., et al., "The effect of sleep onset on upper airway muscle activity in patients with sleep apnoea versus controls", Feb. 2005, vol. 564, Part 2, pp. 549-562, https://www.ncbi.nlm.nih.gov/pmc/articles/PMC1464430/.

Pengo, M.F., et al., "Emerging technology: electrical stimulation in obstructive sleep apnoea", Aug. 2015, vol. 7, Issue 8, pp. 1286-1297, https://www.ncbi.nlm.nih.gov/pmc/articles/PMC4561275/.

Isono, S., et al., "Effects of tongue electrical stimulation on pharyngeal mechanics in anesthetized patients with obstructive sleep apnoea", European Respiratory Journal, Dec. 1999, vol. 14, Issue 6: pp. 1258-1265, https://erj.ersjournals.com/content/erj/14/6/1258.full.pdf.

\* cited by examiner

APPARATUS AND METHOD FOR TREATING OBSTRUCTIVE SLEEP APNEA

CROSS REFERENCE TO RELATED APPLICATION

This application is related to and claims the benefit of U.S. Provisional Patent Application No. 62/922,341, filed Aug. 5, 2019, entitled Pulse Oximeter Control of Transcutaneous Electrical Stimulation (TES) Upper Airway ("the Provisional Application"), the entirety of which is incorporated herein by reference. The incorporation by reference of the Provisional Application is limited such that any definitions provided therein are not incorporated by reference herein unless expressly included herein. In the event of inconsistent usages between the instant application and the Provisional Application, the usage in the Provisional Application should be considered supplementary to that of the instant application; for irreconcilable inconsistencies, the usage in the instant application controls.

FIELD OF THE DISCLOSURE

The present invention relates generally to treating obstructive sleep apnea (OSA) using transcutaneous electrical stimulation ("TES"), and more specifically to an apparatus and method that uses pulse oximetry data to control TES applied to certain nerves and muscles in a person's upper airway to treat OSA. In other embodiments, pulse oximetry data is used to control a continuous positive airway pressure ("CPAP") or autopap machine alone, or in combination with TES, to treat OSA.

BACKGROUND OF THE DISCLOSURE

OSA is a cessation of breathing caused by an obstruction of the upper airway during sleep. The obstruction during OSA is usually intermittent and occurs repeatedly in sleep, and results in decreased oxygen levels. In patients with moderate to severe OSA, it is common to prescribe the use of a CPAP or autopap (hereinafter collectively "CPAP") machine to keep the upper airway open during sleep. However, CPAP is generally not well tolerated due to one or more of: feelings of claustrophobia from a mask; the feeling of wind blowing in the person's face; the swallowing of air; smells in the mask; face soreness; dry nose; congested mouth; and, machine noise. In patients with mild OSA, oral appliances may be prescribed, but they suffer from other problems that cause them to be intolerable. Surgical treatments are also known, but, in addition to being invasive, are painful, expensive, reveal high morbidity, and at best work 50 percent of the time. The primary surgery, uvulopalatopharyngoplasty ("UPP") may decrease the size of the upper airway making sleep apnea worse, further decreasing the resting tone of the upper airway during sleep. Other types of surgery cause problems as well.

Accordingly, a non-invasive, well tolerated, treatment for OSA is desired.

SUMMARY OF THE DISCLOSED EMBODIMENT

According to one embodiment, a non-invasive method and apparatus for treating OSA employs TES that is controlled by data indicative of blood oxygen level provided by a pulse oximeter. TES is applied to one or more muscles and/or nerves of a person's upper airway, such as to the hypoglossal nerve, tongue muscles (genioglossus and geniohyoid), submental muscles, anterior neck muscles, and/or jaw muscles (e.g., masseters) (collectively "the controlled nerves/muscles"), when the person's blood oxygen level falls below a predetermined threshold, such as 90 percent, as measured by the pulse oximeter. When the person is sleeping, the applied TES aids in the movement of the tongue, thus opening the airway while allowing the person to remain remaining asleep. Electrodes, that are in communication with a source of TES, such as a transcutaneous electrical stimulation (TENS) device, are applied to the person's skin, beneath the jaw, so as to provide the TES to the controlled nerves/muscles, based on the blood oxygen data provided by the pulse oximeter. The application of TES is controlled via a controller according to a program that may be wirelessly downloaded (e.g., via Bluetooth or WiFi) from a smart phone equipped with an appropriate programming app.

In another embodiment, pulse oximeter data is used to control the operation of a CPAP machine, such that the CPAP machine's setting is varied based on the data from the pulse oximeter, to treat OSA. In yet another embodiment, pulse oximeter data is used to control both the application of TES, as noted above, and the operation of a CPAP machine.

DETAILED DESCRIPTION OF THE DISCLOSED EMBODIMENTS

Figure 1:
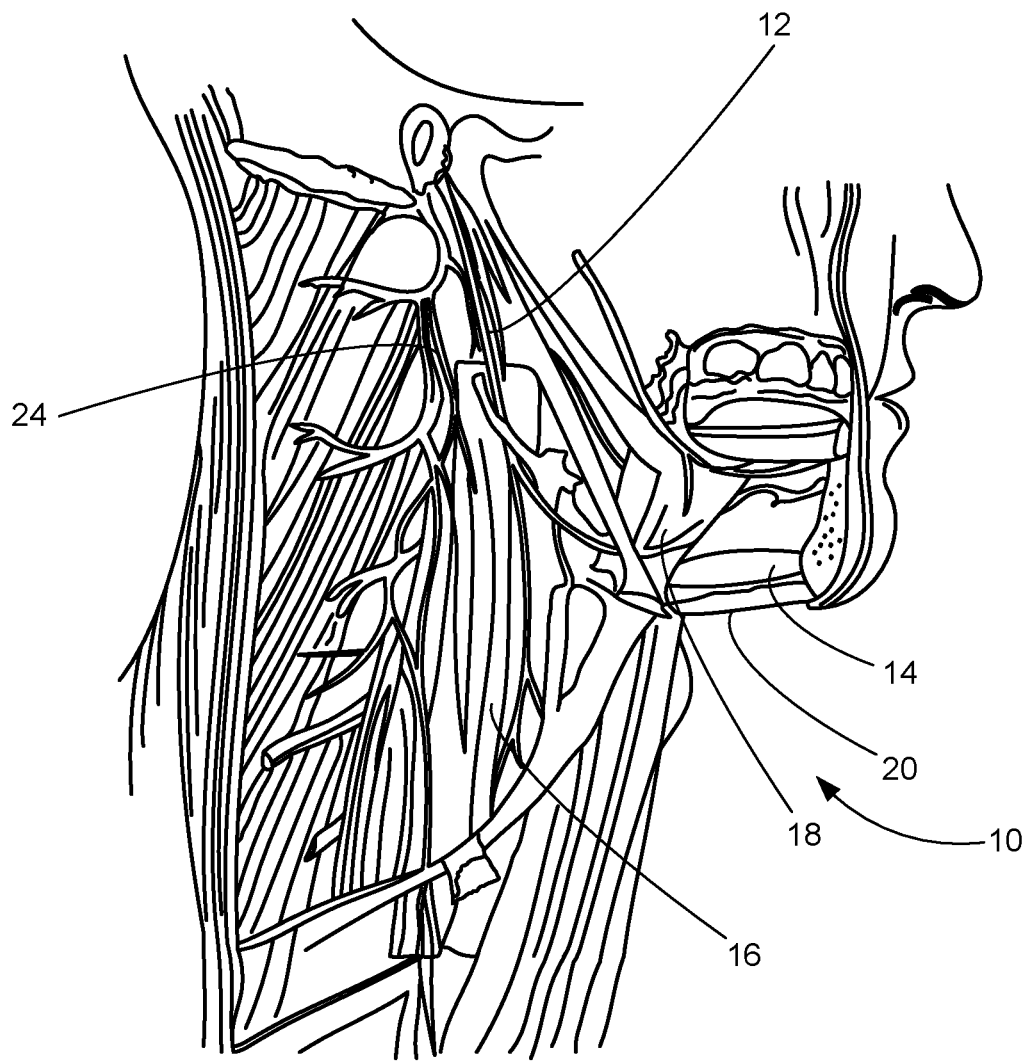
FIG. 1 illustrates relevant parts of the human upper airway.
Figure 2:
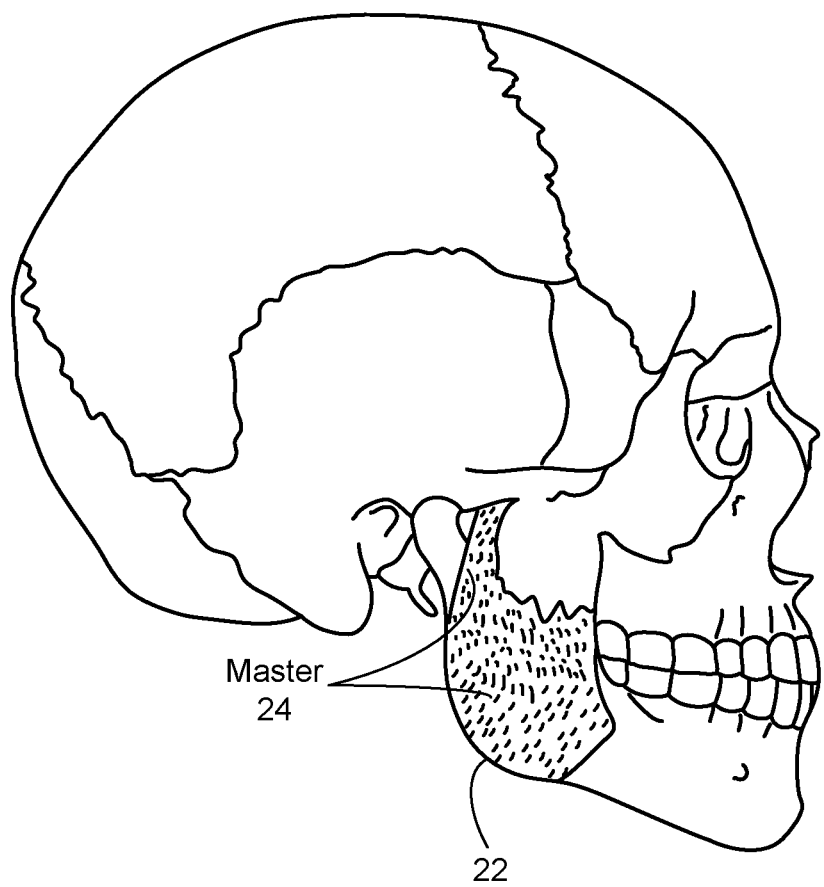
FIG. 2 illustrates the masseter and posterior jaw region.
Figure 3:
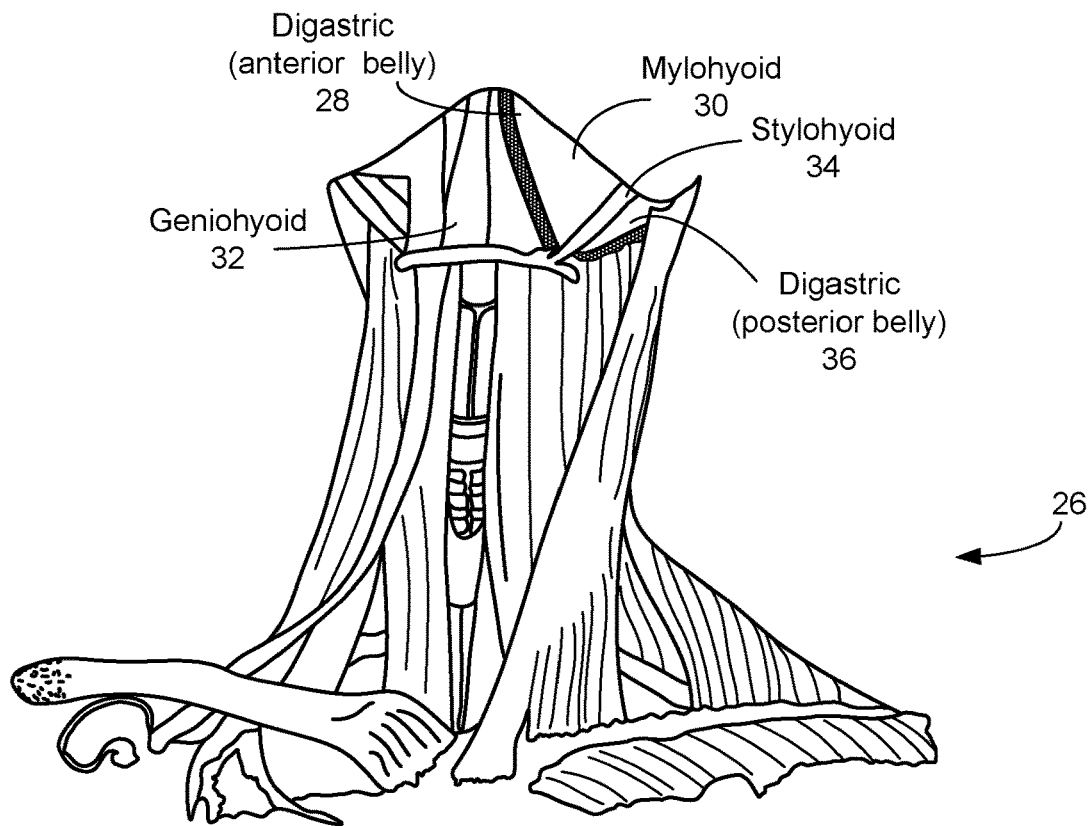
FIG. 3 additional details of the human upper airway.

Referring now to the drawings, wherein like numerals represent like elements, there is shown in FIG. 1 the anatomy of a human's jaw and upper airway region 10. Specifically, relevant to the instant disclosure are the hypoglossal nerve 12, the genioglossus 14, the common internal and external carotid 16, the submandibular 18, the submental jaw region 20, the posterior jaw region and the masseter region 24. FIG. 2 more specifically illustrates the posterior jaw region 22 and masseter region 24. FIG. 3 illustrates further details of a human upper airway region 26, including the digastric (anterior belly) muscle 28, the mylohyoid muscle 30, the geniohyoid muscle 32, the stylohyoid muscle 34, and the digastric (posterior belly) muscle 36. All of the foregoing represent nerves/muscles that may undergo TES in connection with the practice of the present invention, and thus represent, individually and collectively, "the controlled nerves/muscles".

As is known by those skilled in the art, stimulating various regions of the controlled nerves/muscles aids in preserving the resting tone and or movement of the tongue and opens a person's airway so as to prevent interrupted sleep due to airway obstructions that occur during the onset of OSA, and to prevent oxygen levels in the blood to drop.

Figure 4:
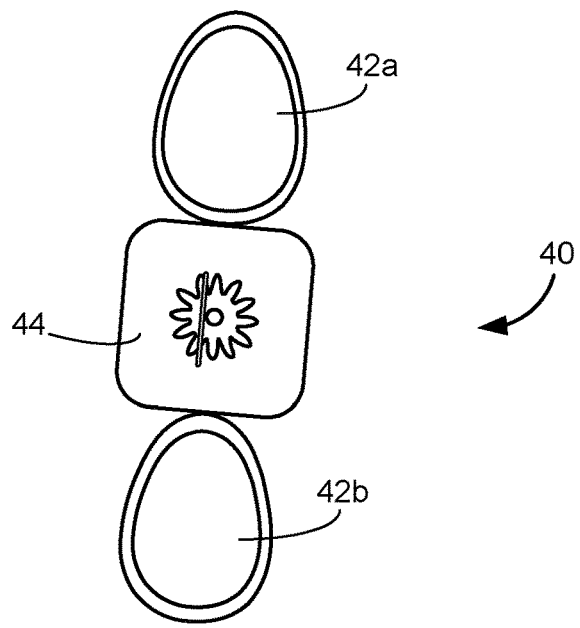
FIG. 4 illustrates an apparatus for applying TES to the skin adjacent a person's upper airway.

FIG. 4 illustrates an embodiment of an apparatus 40 that may be employed to stimulate the controlled nerves/muscles in a manner further described herein. The apparatus 40 includes a pair of electrodes 42a, 42b (collectively bipolar electrodes) connected to a source of electrical stimulation 44, such as a TENS device. As described below, the electrical stimulation source 44 is selectively activated to stimulate the controlled nerves/muscles in accordance with data from a pulse oximeter that is indicative of the person's blood oxygen level.

Figure 5:
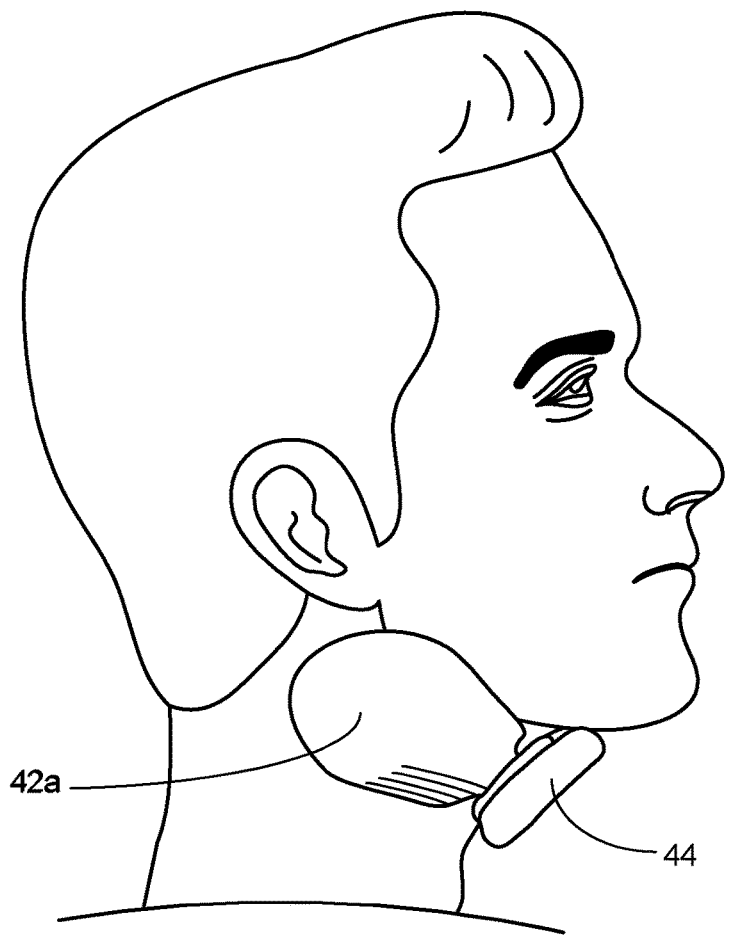
FIG. 5 illustrates application of the apparatus of FIG. 4 to the skin adjacent a person's upper airway.

FIG. 5 illustrates placement of the apparatus 40 to a person's skin over the upper airway region according to one embodiment. As shown, the apparatus 40 is placed such that the electrodes 42 stimulate one or several of the controlled nerves/muscles by the application of TES delivered via the electrical stimulation source 44. Preferably, the electrodes 42 have a replaceable adhesive gel type coating over each electrode that easily adhere to, and are easily removed from, the skin. The skin may be prepared with alcohol wipes. The electrodes 42 may be applied halfway between the chin and the angle of the mandible as well as over the submandibular and submental areas to deliver TES on each side. As discussed below, the electrical stimulation source 44 may include a controller for controlling the application of electrical stimulation according to program code stored in the controller based on data indicative of the person's blood oxygen.

Figure 6:
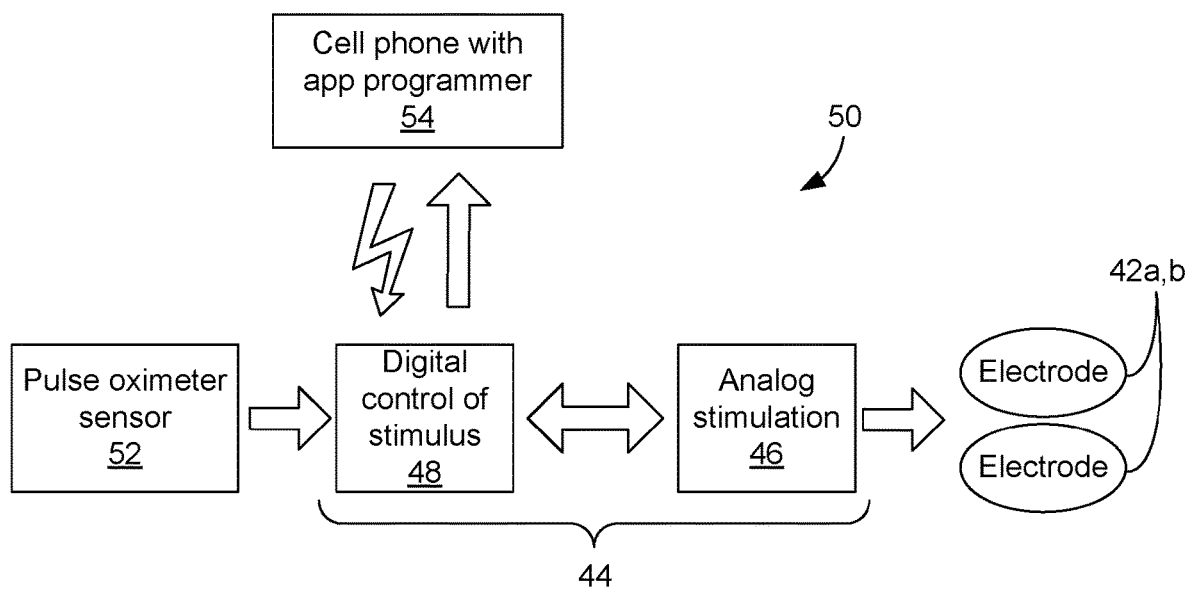
FIG. 6 illustrates a block diagram of an embodiment of a system for controlling and applying TES as disclosed herein.

In the embodiment illustrated in FIG. 6, apparatus 44 comprises a source of TES 46 (e.g., a TENS device) and a controller 48 for controlling the application of TES to the electrodes 42. The controller communicates with a pulse oximeter 52 so as to receive data indicative of the person's blood oxygen level. Pulse oximeter 52 continuously measure the person's blood oxygen level in well know fashion. The pulse oximeter may be integrated with the apparatus 44 (so as to measure blood oxygen at the location of the apparatus 44 relative to the skin) or may be separate therefrom (e.g., applied to a person's finger or wrist etc.). In some embodiments, the controller 48 contains all of the structure, e.g., processor, code, interface etc., needed to carry program the controller and carry out the functionality described herein. In other embodiments, the controller communicates with a smart phone 54, via Bluetooth, WiFi or other appropriate wireless connections. An app may be downloaded to the smart phone 54 for programming the controller 48 to carry out the functionality disclosed herein, or to communicate with the controller 48 in real time to control the electrical stimulation source 46. The system of FIG. 6 is referred to generally by reference numeral 50.

The controller 48 controls the voltage, pulse duration, shape and frequency of an analog stimulation signal applied to the electrodes 42 by the source of the TES. For example, most TENS devices are voltage based because the impedance or resistance at the electrode-skin interface increases as the electrode dries out or loses contact with the skin. Therefore voltage-regulated stimulation output may be used to avoid burning the skin. (Electrode impedance increases according to ohms law, therefore the current delivered with a voltage-regulated stimulator decreases, thus minimizing high current densities). The program stored in the controller 48 may be altered (e.g., via the app in the smart phone) to allow for changes to burst rate, voltage, polarity, wave shape, inversion etc. of the analog signal provided by the TENS device. In one embodiment, the controller is programmed to deliver TES when blood oxygen falls below 90%, and no TES is delivered when blood oxygen is above 90%.

Prior to prescribing treatment for sleep apnea, the person is permitted to fall asleep, and apnea is determined from a split night study (see below), and if the oxygen saturation drops below a predetermined threshold, e.g., 90%, the controller may deliver stimulation that is increased over a time interval, e.g., one minute, until the level of comfort, as recorded while the person was awake (see below) was reached or until the person's blood oxygen rises to or above the predetermined threshold.

Figure 7:
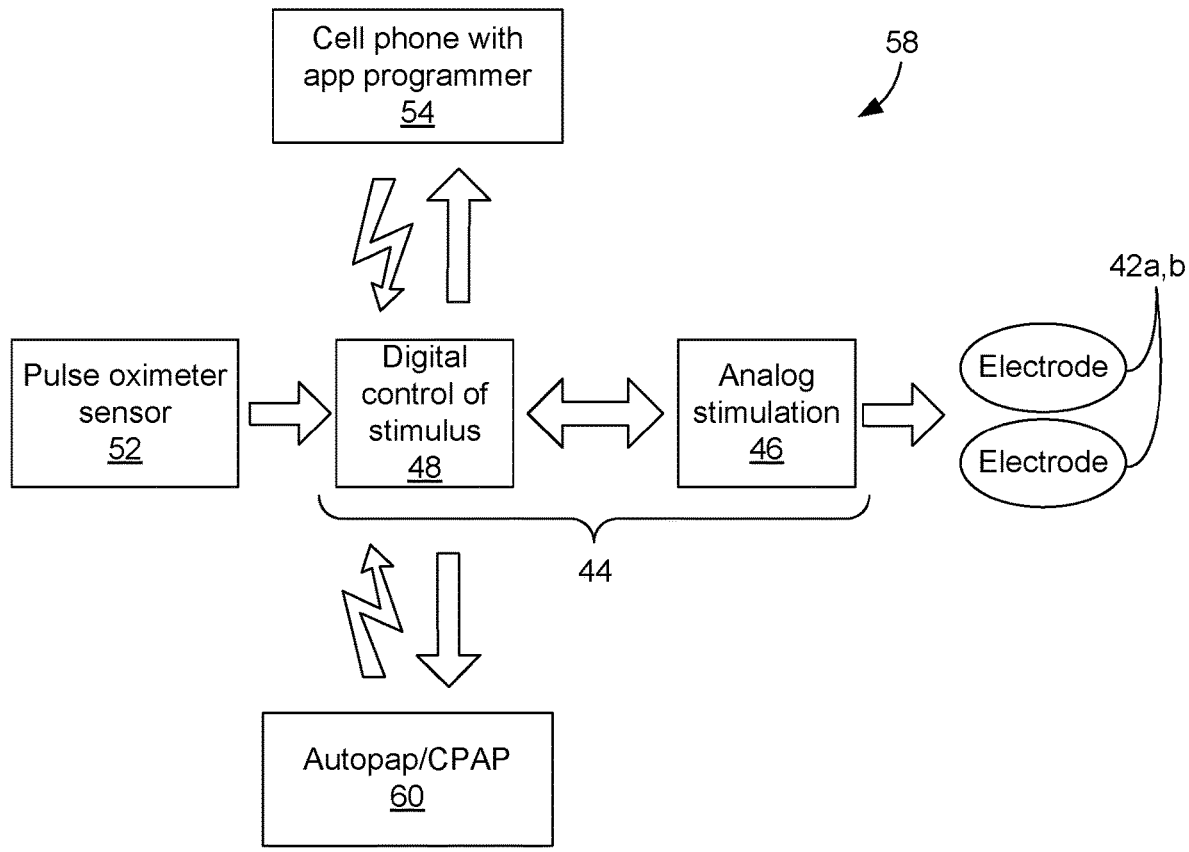
FIG. 7 illustrates a block diagram of an embodiment of a system for controlling and applying TES and controlling a CPAP machine as disclosed herein.
Figure 10:
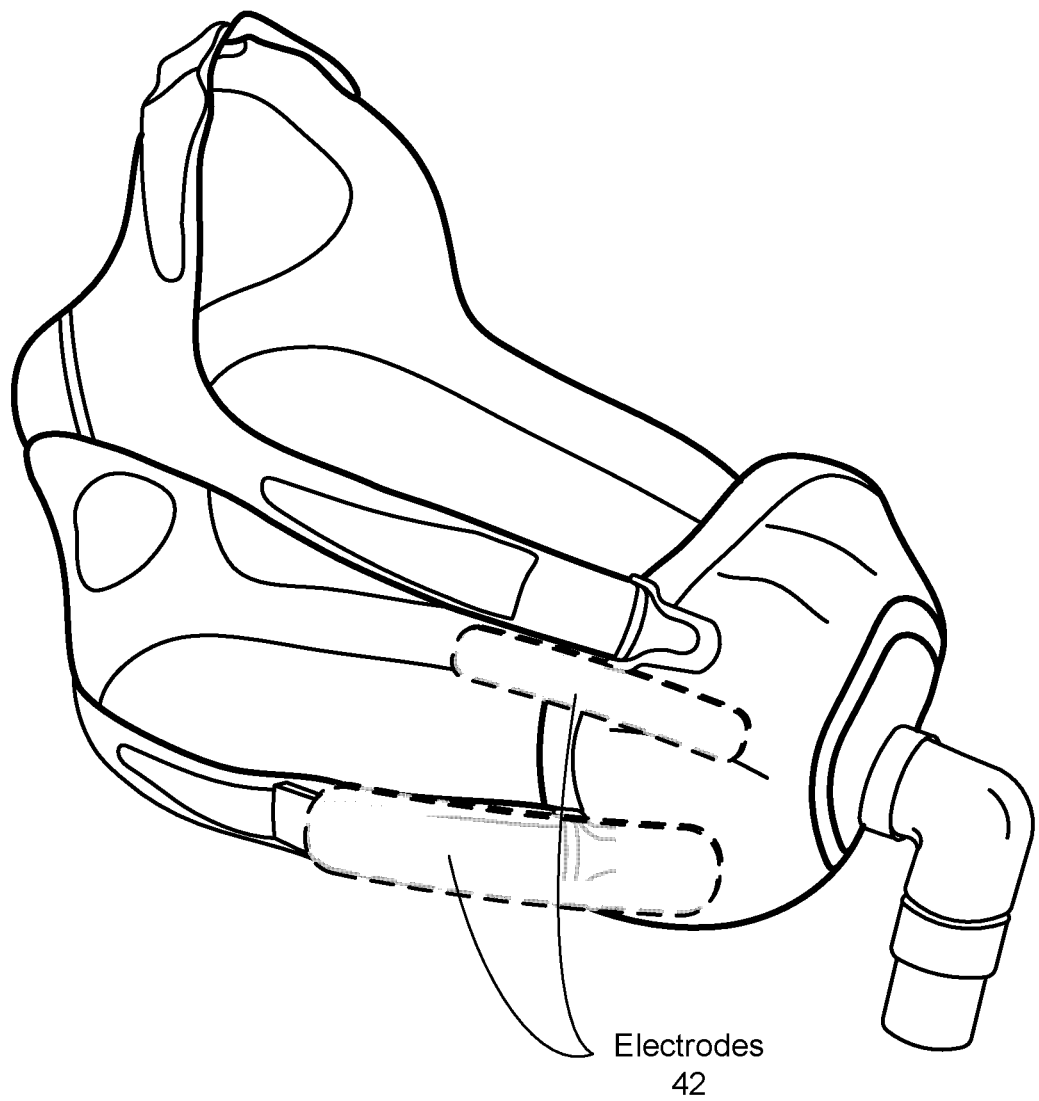
FIG. 10 illustrates an embodiment of a CPAP mask having integrated electrodes for applying TES as described herein.

The system 50 may be used alone, as described above, or in conjunction with a CPAP machine. For example, as shown in FIG. 7, the system referred to generally by reference numeral 58, is similar to that of the system of FIG. 6, except that it also incorporates a CPAP machine 60. TES stimulation and CPAP operation are controlled by the controller to turn TES stimulation and the CPAP machine on and off based on the person's blood oxygen level. As shown in FIG. 10, in this embodiment the electrodes 42 may be integral with the CPAP mask.

Figure 8:
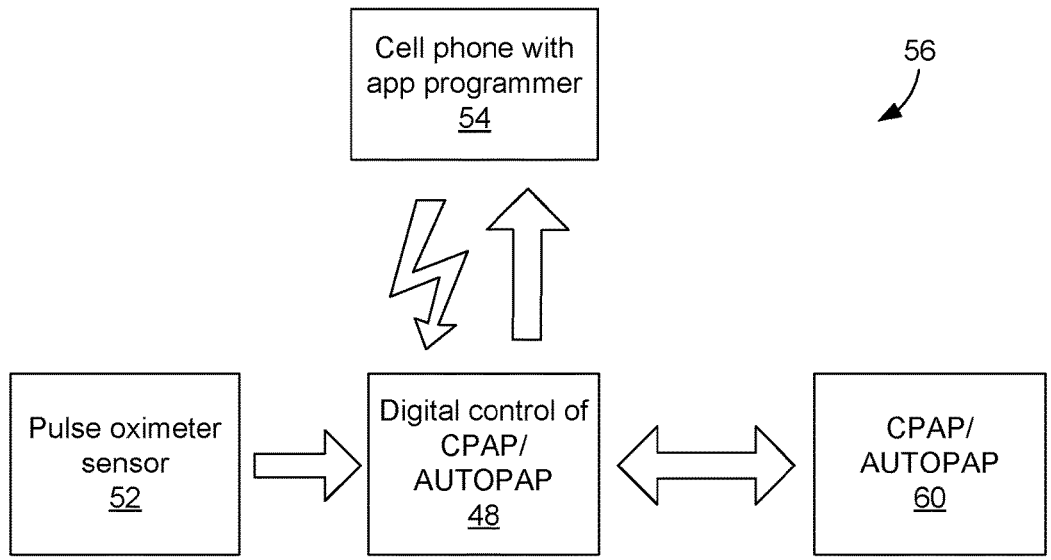
FIG. 8 illustrates a block diagram of an embodiment of a system for controlling a CPAP machine as disclosed herein.

In another embodiment, the blood oxygen level data is employed to control the operation of only a CPAP machine. As shown in FIG. 8, the controller 48' (specifically programmed to control a CPAP machine 60 rather than a source of TES) receives blood oxygen data from pulse oximeter 52, and operates in accordance with program code stored therein. In some embodiments, the controller 48' contains all of the structure, e.g., processor, code, interface etc., needed to program the controller and carry out the functionality described herein. In other embodiments, the controller communicates with a smart phone 54, via Bluetooth, WiFi or other appropriate wireless connections. An app may be downloaded to the smart phone 54 for programming the controller 48' to carry out the functionality disclosed herein, or to communicate with the controller 48' in real time to control the CPAP machine 60. The system of FIG. 8 is referred to generally by reference numeral 56.

Figure 9:
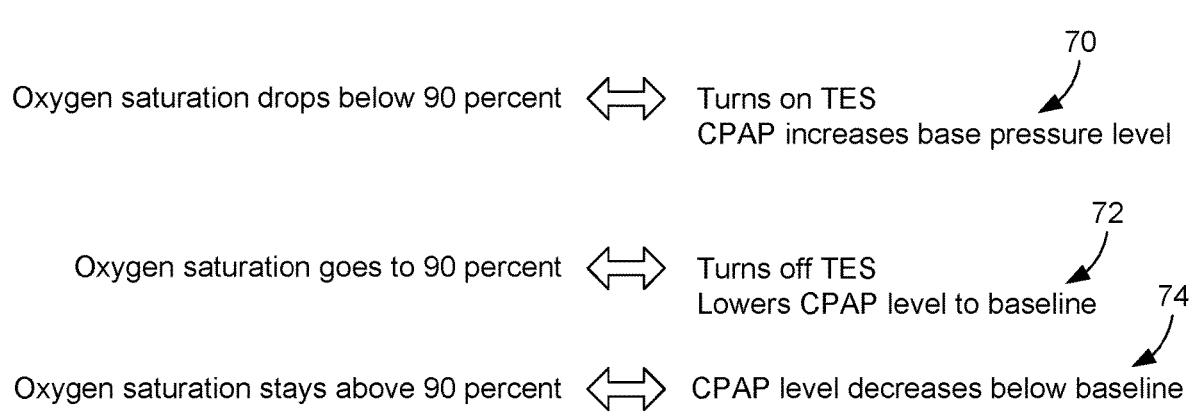
FIG. 9 illustrates one embodiment of the operation of the systems disclosed herein.

One embodiment of the functionality of systems 50, 56 and 58 is shown generally in FIG. 9. As shown at 72, if the blood oxygen drops below 90%, TES is applied, and, if a CPAP is also being used, the CPAP base pressure is increased. As shown at 74, of the blood oxygen goes to 90%, the TES is removed and the CPAP baseline pressure is reduced. As shown at 74, if the blood oxygen remains above 91%, TES is removed and the CPAP base pressure is permitted to drop to make the CPAP more tolerable to the person.

In another embodiment, if the person's blood oxygen continues to decrease while TES is applied, the amount of stimulation (voltage) may be increased, and other TES parameters (e.g., pulse width, frequency, etc.) may be adjusted.

In practice, the amount of stimulation to be applied may be tested and determined while the person is awake so as to determine a comfortable level of the maximum tolerable level of stimulation that will prevent arousal from sleep. Daytime fatigue symptoms may be assessed by the Epworth Sleepiness Scale. BMI and age may be recorded. Neck circumference of patients may also be measured. Before full polysomnography, it may be determined that a person does not have upper airway obstruction when supine and awake at the start of the study. The sleep study may be performed when the patient goes to bed. Polysomnography may be performed with split night study so that persons with OSA have a way to compare effects with and without TES, and to identify stimulation settings, e.g., current, voltages, pulse duration, shape, and frequency.

There has thus been described an apparatus and method that employs TES for a combination of neuro and muscle stimulation of the muscles and nerves to keep a person's upper airway open during hypoxia from OSA. The apparatus and method described herein may be embodied in other specific forms without departing from the spirit or essential attributes thereof. Accordingly, reference should be made to the appended claims, rather than the foregoing specification, for indicating the scope of the invention.

What is claimed is:

1. An apparatus comprising a pulse oximeter, a source of transcutaneous electrical stimulation (TES) having a pair of electrodes for delivering TES to a person, the electrodes being adapted to be applied to a surface of the person's skin adjacent the person's upper airway and to non-invasively stimulate one or more nerves or muscles only in the person's upper airway when TES is applied to the electrodes, and a controller adapted to receive blood oxygen data from the pulse oximeter, the controller being programmed to generate a signal that applies TES when the blood oxygen data indicates that the person's blood oxygen is below a predetermined threshold, so as to increase a resting tone of the person's tongue solely in response to the indication that the person's blood oxygen is below the predetermined threshold, the controller being adapted to wirelessly receive program instructions from a smart device equipped with an app for specifying, via the app, characteristics of the TES including at least one of burst rate, voltage, polarity, wave shape and inversion of the signal, such that one or more of the characteristics may be wirelessly adjusted via the app.

2. The apparatus according to claim 1 wherein the predetermined threshold is 90%.

3. The apparatus according to claim 1 wherein the pulse oximeter, the source of TES and the controller are integrated as a single unit.

4. The apparatus according to claim 1 wherein the controller is further programmed to control a continuous positive airway pressure (CPAP) machine having a mask, and to regulate an air pressure supplied by the CPAP machine to the mask based solely upon the blood oxygen data.

5. The apparatus according to claim 1 further comprising a continuous positive airway pressure (CPAP) machine having a mask, and the controller is programmed to regulate an air pressure supplied by the CPAP machine to the mask based solely upon the blood oxygen data.

6. The apparatus according to claim 5 wherein the electrodes are integrated with the mask.

* * * * *